United States Patent [19]

Collins

[11] Patent Number: 5,444,092

[45] Date of Patent: Aug. 22, 1995

[54] METHOD AND COMPOSITION FOR TREATING PSORIASIS

[76] Inventor: Jerry Collins, 401 Ocean Bluffs Blvd., #101, Jupiter, Fla. 33477

[21] Appl. No.: 279,804

[22] Filed: Jul. 20, 1994

[51] Int. Cl.$^6$ .................. A01K 7/00; A01K 31/00
[52] U.S. Cl. .................... 514/560; 514/724; 514/558; 514/568; 514/969; 514/943; 514/844; 424/78.03
[58] Field of Search ............... 514/310, 560, 724, 558, 514/568, 969, 943, 844; 424/78.03

[56] References Cited

U.S. PATENT DOCUMENTS

| | | | |
|---|---|---|---|
| 4,199,576 | 4/1980 | Reller et al. | 514/159 |
| 4,276,430 | 6/1981 | Reller et al. | 560/66 |
| 5,002,767 | 3/1991 | Masse | 424/195.1 |
| 5,006,337 | 4/1991 | Motitschke et al. | 424/195.1 |
| 5,057,500 | 10/1991 | Thornfeldt | 514/53 |
| 5,106,879 | 4/1992 | Clark | 514/724 |
| 5,122,514 | 6/1992 | Boger et al. | 514/19 |
| 5,165,932 | 11/1992 | Horvath | 424/195.1 |
| 5,171,581 | 12/1992 | Smith | 424/617 |
| 5,176,912 | 1/1993 | Cabezas | 424/94.63 |
| 5,179,086 | 1/1993 | Flender | 514/12 |
| 5,190,917 | 3/1993 | Lezdey | 514/12 |
| 5,242,905 | 9/1993 | Blank | 514/19 |

*Primary Examiner*—Arthur C. Prescott
*Attorney, Agent, or Firm*—McHale & Slavin

[57] ABSTRACT

A novel skin lotion consisting of a mixture of lye, oils, alcohol, coal tar, and menthol U.S.P. The mixture provides a cleansing lotion that readily treats psoriasis. When the mixture is applied to the skin, the lye provides a soap for cleansing and the base oil operates to soften and moisturize the skin. The use of a coal tar solution including alcohol penetrates the dermis of the skin to reduce inflammation. The addition of menthol U.S.P. helps cool the affected area and lessens itching.

5 Claims, No Drawings

METHOD AND COMPOSITION FOR TREATING PSORIASIS

FIELD OF THE INVENTION

This invention relates to a method for treating psoriasis, namely, a treatment that provides for cleaning and soothing of affected areas to facilitate healing.

BACKGROUND OF THE INVENTION

Psoriasis is a chronic recurring disease of the skin characterized by the appearance of plaques, patches, or papules on the skin surface. Deletions are elevated above the skin surface and they are red to a reddish brown in color making them clearly distinguishable from the normal skin. Due to their slightly elevated status they can be easily scraped off leaving bleeding points. The extent of the disease may vary from a few lesions to a generalized involvement of most of the skin. Characteristically the portions of the body affected are the elbows, knees, scalp and chest.

The cause of the disease is unknown but as a disease of the epidermis it is a major disability for nearly ten million persons in the United States alone. Since the cause of the disease is unknown, the treatment thereof remains the province of dermatologists.

In severe cases of chronic psoriasis, a well known treatment includes coating the skin with a dye that absorbs ultra-violet light followed by shining an ultra-violet light on the coated area. The problem with such a treatment is that a technique has been found to increase the incidents of mild skin cancers thus limiting its use to severe cases.

Numerous medicated skin lotions have also been presented which involve various therapeutic uses as well as moisturizing of the skin. It is further known that maintaining the area in a clean state lessens infection, however, constant washing can leave the skin dry. Known prior art to the inventor sets forth a number of methods of treating psoriasis which may show one of the present invention ingredients but not all of the ingredients of the novel lotion of the instant invention. Such prior art includes U.S. Pat. Nos. 5,106,879; 5,122,514; 5,165,932; 5,171,581; 5,176,912; 5,179,086; 5,190,917; 5,242,905. Many medicated treatments must be approved by a medical doctor and may cause allergic reactions in some individuals.

What is needed is a treatment for psoriasis that is inexpensive to produce, operates to cleanse the skin providing a conditioner for healing and cooling to be applied thus facilitating the treatment of psoriasis.

SUMMARY OF THE INVENTION

Disclosed is a novel skin lotion consisting of a mixture of lye, oils, alcohol, coal tar, and menthol. The recipe produces an inexpensive mixture that readily treats psoriasis by maintaining an affected area in clean, soft, and slightly coated state. When the mixture is applied to the skin, the lye produces a soap lather for cleansing. An oil base of fatty acids operates to soften and moisturize the skin. The use of a coal tar solution having alcohol, polysorbate and coal tar penetrates the dermis of the skin and operates to reduce inflammation. The addition of menthol U.S.P. helps cool the affected area and lessens itching.

Thus, a primary objective of the instant invention is to disclose an inexpensive lotion that has been found extremely effective in the treatment of psoriasis without the need for medical prescription.

Still another objective of the instant invention is to disclose a modified embodiment of said lotion that can be used for maintenance of an affected area.

Other objects and advantages of this invention will become apparent from the following description.

DETAILED DESCRIPTION OF THE INVENTION

Although the invention is described in terms a specific embodiment, it will be readily apparent to those skilled in this art that various modifications, rearrangements and substitutions can be made without departing from the spirit of the invention. The scope of the invention is defined by the claims appended hereto.

The base of the novel skin lotion of the present invention consists of a surfactant for cleansing and a base oil softening and moisturizing of the skin. The base oil can be assimilated to peanut or soybean oil admixed with water, the preferred base oil would include the following composition of fatty acids:

| | |
|---|---|
| Palmitic | 5.5% |
| Palmitoleic | .4% |
| Stearic | .6% |
| Oleic | 46.8% |
| Linoleic | 40.5% |
| Linolenic | .9% |
| Arachidic | 2.3% |
| Behenic | 2.9% |

Oleic acid operates as an antiphlogistic. Linoleic acid operates to as a smoothing agent. The combination is added to water and then mixed with a small amount of sodium hydroxide or potassium hydroxide, lye, to produce a homogenous emulsion having a syrupy consistency. Application of the mixture to an affected area provides a ready lather that operates to cleanse, soften, and moisturizes the skin thus providing for inexpensive maintenance of affected areas.

Treatment of the affected area further calls for the addition of aforementioned base with the following active ingredients to penetrate into the dermis:

| | |
|---|---|
| Alcohol | 75% |
| Polysorbate | 5% |
| Coal tar | 20% |

The ingredients enter the dermis of the skin lessening the lesions leading to infection and provides a coating of the skin's surface. Coal tar slows cell reproduction providing a healing period for the affected area. A premix solution of coal tar can be obtained without prescription, commonly known as coal tar U.S.P. Menthol U.S.P. is a mild rubefacient added to the solution providing a cooling affect to the skin to lessen itching typical of psoriasis.

The present invention is of the discovery that a person having the disease of psoriasis may enjoy a disappearance or lessening of the symptoms. Use of the instant skin lotion is by applying it to the affected area in a manner so as to cleanse the skin followed by removal of the solution by rinsing the area with water before a second application is placed on the skin in a lightly coated manner so as to act as treatment to the lesions.

The application should be applied in the morning and evening, preferably before sleep.

In a completed mixture, the base of oil, lye and water makes up approximately 80% of the mixture while the coal tar solution and menthol U.S.P. each form equal portions of approximately 10% for the remainder of the solution. The solution is mixed by placement of the menthol U.S.P. crystals in the coal tar solution wherein the alcohol will dissolve the crystals with minimal mixing. The solution is then added to the base solution to prepare the total skin lotion. In instances where cell reproduction is not a concern then the coal tar and alcohol can be removed and the menthol U.S.P. crystals mixed with a small amount of alcohol to dissolve into a liquid solution which is then added to the base solution forming a clear gel. The gel operates in a similar manner to the aforementioned process wherein the solution is applied to the affected area in the morning and evening for optimum results. It is recommended that the coal tar solution does not exceed 10% of the total solution when added from the premixed combination of alcohol, polysorbate and coal tar as found in coal tar U.S.P.

It is to be understood that while I have described certain forms of my invention, it is not to be limited to the specific forms or arrangement herein describe. It will be apparent to those skilled in the art that various substitutions may be made without departing from the scope of the invention and the invention is not to be considered limited to what is described in the specification.

What I claim is:

1. A novel skin lotion admixed with water comprising the following ingredients:

| | |
|---|---|
| palmitic | 5.5% |
| palmitoleic | .4% |
| stearic | .6% |
| oleic | 46.8% |
| linoleic | 40.5% |
| linolenic | .9% |
| arachidic | 2.3% |
| behenic | 2.9% |

2. The skin lotion according to claim 1 including the following ingredients:

| | |
|---|---|
| alcohol | 75% |
| polysorbate | 5% |
| coal tar | 20% |

3. The skin lotion according to claim 1 including the following ingredients: an oil base forming approximately 80 percent of said lotion; a coal tar mixture forming approximately 10 percent of said lotion; and menthol U.S.P. forming approximately 10 percent of said lotion.

4. The lotion according to claim 1 wherein said oil base is formed from a mixture of water and fatty acids consisting of approximately 5.5% palmitic, 0.4% palmitoleic, 0.6% stearic, 46.8% oleic, 40.5 linoleic, 0.9% linolenic, 2.3% arachidic, and 2.9% behenic.

5. The lotion according to claim 1 wherein said coal tar solution is formed from a mixture of 75% alcohol, 5% polysorbate, and 20% coal tar.

* * * * *